United States Patent [19]

Miklean et al.

[11] Patent Number: 5,705,145
[45] Date of Patent: Jan. 6, 1998

[54] SKIN TANNING COMPOSITIONS AND METHOD

[75] Inventors: Saul Miklean, Floral Park, N.Y.; Konstantinos M. Lahanas, Paramus, N.J.; Nicolae Vrabie, Jackson Heights, N.Y.; Edward Pelle, Valley Stream, N.Y.; Andrew J. Bevacqua, E. Setauket, N.Y.

[73] Assignee: E-L Management Corp., New York, N.Y.

[21] Appl. No.: 697,230

[22] Filed: Aug. 21, 1996

[51] Int. Cl.$^6$ .............................. A61K 7/42; A61K 7/02
[52] U.S. Cl. .............................. 424/59; 424/63; 424/69; 514/938
[58] Field of Search .............................. 424/59, 69, 63; 514/938, 844, 847, 944

[56] References Cited

U.S. PATENT DOCUMENTS

| | | | |
|---|---|---|---|
| 2,949,403 | 8/1960 | Andreadis et al. | 167/90 |
| 3,177,120 | 4/1965 | Black et al. | 167/90 |
| 4,228,151 | 10/1980 | Lang et al. | 424/60 |
| 4,293,542 | 10/1981 | Lang et al. | 424/47 |
| 4,434,154 | 2/1984 | McShane | 424/60 |
| 4,708,865 | 11/1987 | Turner et al. | 424/59 |
| 5,229,104 | 7/1993 | Sottery et al. | 424/59 |
| 5,232,688 | 8/1993 | Ziegler et al. | 424/59 |
| 5,252,322 | 10/1993 | Stoner et al. | 424/59 |
| 5,318,774 | 6/1994 | Alban et al. | 424/59 |
| 5,514,367 | 5/1996 | Lentini | 424/59 |
| 5,560,917 | 10/1996 | Cohen | 424/401 |

OTHER PUBLICATIONS

The Journal of Investigative Dermatology, Goldman, et al. (1990) pp. 161–164.
J. Soc. Cosm. Chem., Bobin, et al. (1984) 35, pp. 265–272.

Primary Examiner—Alan L. Rotman
Assistant Examiner—Evelyn Huang
Attorney, Agent, or Firm—Karen A. Lowney, Esq.; Isaac D. Cohen, Ph.D.

[57] ABSTRACT

Disclosed are cosmetic compositions for providing an artificial tan to skin which comprise dihydroxyacetone and an azole in a cosmetically or pharmaceutically acceptable carrier. Also disclosed is a method for providing an artificial tan to skin which comprises applying dihydroxyacetone and an azole to the skin.

38 Claims, No Drawings

SKIN TANNING COMPOSITIONS AND METHOD

FIELD OF THE INVENTION

This invention relates to cosmetic compositions for providing an artificial tan to skin and a method for their use. More specifically, the invention relates to skin tanning compositions which comprise dihydroxyacetone and an azole in a cosmetically or pharmaceutically acceptable carrier, as well as to a method of providing an artificial tan to human skin which comprises applying dihydroxyacetone and an azole to the skin.

BACKGROUND OF THE INVENTION

Many individuals have a skin complexion which does not tan readily on exposure to sunlight. Others achieve a tan only following a period of great discomfort, sunburn and possibly other adverse effects to the skin due to exposure to the sun's rays. Yet attainment of a tan by many individuals is highly desired for cosmetic and other reasons, especially if this can be accomplished without the usual exposure to the sun, i.e., through skin tanning agents.

In other instances, individuals who tan with difficulty may desire to extend the life of a naturally acquired tan without re-exposure to the sun. Also, a skin tan may be desired when weather conditions do not permit the sun exposure necessary to acquire a tan.

Acquisition of a natural tan by exposure to the sun, however, may be almost impossible for those very light skinned persons who tend to burn rather than tan. In addition, the deleterious effects of excessive exposure to sunlight are becoming more generally recognized.

It is known in the art that an artificial tan can be achieved by applying skin tanning agents to the human skin in a suitable vehicle or base. Examples of known skin tanning agents include hydroxyaldehydes such as dihydroxyacetone, also known as DHA; see U.S. Pat. Nos. 2,949,403 to Andreadis et al. and U.S. Pat. No. 5,232,688 to Ziegler et al. Also known as skin tanning agents are imidazole and various imidazole derivatives, such as 4-(hydroxymethyl) imidazole (see U.S. Pat. No. 5,252,322 to Stoner et al.) and pyridine N-oxide and its derivatives (see U.S. Pat. Nos. 4,293,542 to Lang et al. and 4,228,151 to Lang et al.).

U.S. Pat. No. 2,949,403 discloses oleaginous and hydroalcoholic compositions and methods of using DHA as a tanning agent for the human epidermis. U.S. Pat. No. 5,232,688 discloses compositions for self-tanning of skin which include an alpha-hydroxy substituted ketone or aldehyde such as DHA, a polyacrylamide and a pharmaceutically acceptable carrier. DHA is a white, crystalline, hygroscopic powder having the chemical formula $C_3H_6O_3$. When applied topically, DHA is believed to covalently bind to epidermal proteins via their amino groups, producing a cosmetically-acceptable "tan" color; see L. Goldman et al., "Investigative Studies with the Skin Coloring Agents Dihydroxyacetone and Glyoxal," *The Journal of Investigative Dermatology*, 35, 161 (1960), and Bobin et al., "Effects of Color Adjuvants on The Tanning Effect of Dihydroxyacetone," *J. Soc. Cosm. Chem.*, 35, 265 (1984).

Since the 1960's, several compositions using DHA as an active ingredient have been reported (see U.S. Pat. Nos. 4,708,865 to Turner, 5,229,104 to Sottery et al., and 5,318,774 to Alban et al.), as well as compositions containing dihydroxyacetone and sunscreen compounds such as octyl dimethyl PABA (e.g., U.S. Pat. Nos. 3,177,120 to Black et al. and 4,434,154 to McShane).

Further, DHA has been formulated into oil-in-water emulsions, into preparations containing up to 50% alcohol which tend to dry the skin, and into "creamy bases" such as are found in hand and face lotions and creams.

One of the drawbacks associated with the use of DHA as a skin tanning agent is the length of time, generally from 2 to 24 hours, that is required for the DHA to react in the skin to a sufficient extent to produce the desired tanned skin appearance. This is a particularly crucial limitation since activities such as washing, bathing, swimming, as well as sweating, can remove the highly water-soluble DHA from the skin surface before it has had an opportunity to fully react with the skin proteins and amino acids, resulting in an incompletely developed tan. A second drawback is the undesirable orange cast or hue which results from the use of DHA on fair-skinned humans. In some cases dyes such as cutch powder, dogwood powder and walnut powder have been employed to overcome this undesirable cast (see U.S. Pat. No. 4,708,865 to Turner); however, the use of these materials in skin tanning compositions often leads to highly-colored products which are aesthetically unacceptable to consumers.

U.S. Pat. No. 5,252,322 discloses skin tanning compositions containing imidazoles and various imidazole derivatives, such as 4-(hydroxymethyl)imidazole. U.S. Pat. No. 5,252,322 additionally discloses that such compounds are believed to function by stimulating the natural processes in the skin which result in a tan. This patent further discloses several limitations to the use of imidazoles in skin tanning compositions, such as the limited solubility of such compounds in aqueous or alcoholic environments, and the possibility of skin irritation which may result when such compounds are used above certain concentrations.

Further, U.S. Pat. No. 5,252,322 discloses that the above-mentioned imidazole compounds caused visible darkening of the skin of test animals only after lengthy and repeated topical applications, i.e., daily treatments over a period of at least five consecutive days.

There is therefore clearly a need for skin tanning compositions which can provide a natural-looking tan to the skin in a safe and non-irritating manner without the use of dyes. There is also clearly a need for skin tanning compositions which can provide such a tan to the skin in a more rapid and efficient manner than is currently available to the cosmetics consumer.

It is an object of the present invention to provide skin tanning compositions which can provide a natural-looking tan to the skin in a safe, non-irritating, rapid and efficient manner. It is a further object of this invention to provide a method for tanning the skin in a safe, non-irritating, rapid and efficient manner.

These and other objects of the present invention are achieved by incorporating effective amounts of DHA and one or more azoles as skin tanning agents in cosmetic compositions. We believe this invention constitutes the first use of DHA and an azole together as skin tanning agents in such compositions.

It is a surprising and unexpected discovery of the present invention that a combination of DHA and an azole, applied to the skin either substantially simultaneously or sequentially, produces a natural-looking artificial tan on the skin in a much shorter period of time (generally about 30 minutes or less) than has hitherto been possible using DHA alone. It is also a surprising and unexpected discovery that when the azole is an imidazole, the concentration of the imidazole necessary to produce such a tan on the skin is significantly lower than previously known to be needed when the imidazole is employed as the sole skin tanning agent.

SUMMARY OF THE INVENTION

In accordance with the present invention there are provided skin tanning compositions comprising:

(a) dihydroxyacetone;

(b) an azole having the structure

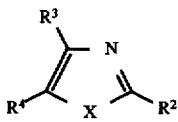

wherein $X=S$, $O$, or $NR^1$, and $R^1$ through $R^4$ can be the same or different and are hydrogen; phenyl; $C_1$–$C_6$ alkyl unsubstituted or substituted by phenyl, hydroxyl, carboxy, benzyloxy, amino, halogen, carboxylic acid, sulfonate or phosphonate; or —$CH_2$—$CH(COOR')NR"R'"$ where $R'$, $R"$ and $R'"$ are the same or different and are hydrogen or $C_1$–$C_4$ alkyl; and (c) a cosmetically or pharmaceutically acceptable carrier.

The invention additionally relates to a method for artificially tanning human skin which comprises applying to the skin dihydroxyacetone and an azole having the structure

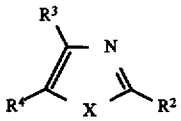

wherein $X=S$, $O$, or $NR^1$, and $R^1$ through $R^4$ can be the same or different and are hydrogen; phenyl; $C_1$–$C_6$ alkyl unsubstituted or substituted by phenyl, hydroxyl, carboxy, benzyloxy, amino, halogen, carboxylic acid, sulfonate or phosphonate; or —$CH_2$—$CH(COOR')NR"R'"$ where $R'$, $R"$ and $R'"$ are the same or different and are hydrogen or $C_1$–$C_4$ alkyl.

The compositions of the present invention are chemically and physically stable, nonirritating and aesthetically pleasing when applied to the skin. They are capable of providing a natural-looking tan to the skin in a safe, rapid and efficient manner.

DETAILED DESCRIPTION OF THE INVENTION

The compositions of the present invention preferably comprise from about 1 to about 20 weight percent, more preferably from about 3 to about 5 weight percent of dihydroxyacetone, by weight of the total composition. The exact amount of dihydroxyacetone employed will vary with the degree of tanning desired, and is readily determined by the skilled artisan. Generally speaking, the higher the concentration of dihydroxyacetone employed in a particular composition, the darker the resultant skin tan color.

The compositions of the present invention additionally comprise an azole having the structure

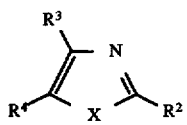

wherein $X=S$, $O$, or $NR^1$, and $R^1$ through $R^4$ can be the same or different and are hydrogen; phenyl; $C_1$–$C_6$ alkyl unsubstituted or substituted by phenyl, hydroxyl, carboxy, benzyloxy, amino, halogen, carboxylic acid, sulfonate or phosphonate; or —$CH_2$—$CH(COOR')NR"R'"$ where $R'$, $R"$ and $R'"$ are the same or different and are hydrogen or $C_1$–$C_4$ alkyl. Preferably the azole is an imidazole, wherein $X=NR^1$, or a thiazole, wherein $X=S$. Most preferably the azole is imidazole itself, wherein $R^1$, $R^2$, $R^3$ and $R^4$ are hydrogen, or a monosubstituted imidazole such as histidine, wherein $R^1$, $R^2$, and $R^3$ are hydrogen and $R^4$ is —$CH_2$—$CH(COOH)NH_2$, or 5-phenylimidazole, wherein $R^1$, $R^2$ and $R^3$ are hydrogen, and $R^4$ is phenyl.

In a preferred embodiment the azole is present in an amount of from about 1.5 to about 7.5 percent by weight, more preferably from about 1.5 to about 2 percent by weight of the total composition.

The compositions of the invention additionally comprise a cosmetically or pharmaceutically acceptable carrier. The term "pharmaceutically or cosmetically acceptable" as used herein refers to materials that are not known to be harmful to humans. These materials can be found for example in the *CTFA International Cosmetic Ingredient Dictionary* 4th Edition, The Cosmetic, Toiletry, and Fragrance Association, Inc., Washington, D.C., 1991, as well as in *Remington's Pharmaceutical Sciences*, 18th Edition, A. R. Greenaro Ed., Mack Publishing Co., Easton, Pa., 1990. Suitable cosmetically or pharmaceutically acceptable carriers for purposes of the present invention include, but are not limited to solutions, especially hydroalcoholic solutions; suspensions; emulsions, especially oil-in-water emulsions, most especially nonionic oil-in-water emulsions; gels, mousses, aerosols and the like. The specific type of carrier used will vary with the desired physical, aesthetic and pharmacological properties of the final composition.

In a preferred embodiment of the present invention the compositions additionally comprise an organic acid, for example an alpha-hydroxyacid such as citric acid or a beta-hydroxyacid such as salicylic acid. It has been found that the incorporation of such an acid into the compositions increases their physical and chemical stability over time, especially when the acid is present in an amount sufficient to lower the pH of the composition to from about 3 to about 5. Without being limited to theory, it is believed that this increase in stability is a result of a physical bond which is formed between the azole and the organic acid in the compositions. Preferably the organic acid is present in the compositions in an amount of about 5 percent by weight of the total composition.

In a preferred embodiment of the invention the compositions additionally comprise one or more antioxidants, which may function in the compositions as stabilizers against oxidative degradation. An especially preferred antioxidant is green tea extract.

The compositions of the present invention additionally may comprise a colloidal mineral dispersion, especially a colloidal dispersion containing ions derived from elements selected from the group consisting of sodium, calcium, titanium, rubidium, lanthanum, yttrium, vanadium, cerium and neodymium. While not being limited to theory, it is believed that such ions act to provide a catalytic platform on which the reaction between the dihydroxyacetone, the azole and the skin can take place. A colloidal mineral dispersion containing, inter alia, the abovementioned ions is available commercially from The Rockland Corporation (Tulsa, Okla.) under the tradename Body Booster, and is especially preferred.

Various other optional ingredients may be included in the compositions of the present invention, including but not limited to emulsifiers, stabilizers, preservatives, emollients, antiseptics, pigments, dyes, humectants, moisturizers, propellants, and sunscreens, as well as other classes of materials whose presence may be cosmetically, or medicinally desirable. Common examples of such ingredients are provided below by way of example and not limitation.

Optional ingredients include emulsifiers such as Peg-100 stearate, glyceryl monostearate, DEA cetyl phosphate, dimethicone copolyol, TEA stearate and the like; ingredients which provide emolliency or humectancy, including polyols such as glycerine and propylene glycol, hydrocarbons such as mineral oil and petrolatum, fatty acid esters such as myristyl lactate and caprylic and capric triglycerides, silicones, and natural whole oils or components thereof, moisturizing ingredients, such as wheat lipid extracts or ceramides, preservatives, such as methyl paraben, butyl paraben, propyl paraben and phenoxyethanol, and mixtures thereof.

In yet another preferred embodiment of the invention the compositions comprise one or more sunscreens. The term "sunscreen" as used herein refers to any material which is capable of protecting human skin from ultraviolet radiation having a wavelength of from about 280 to about 400 nm, by effectively absorbing such radiation, and/or reflecting or scattering such radiation away from the surface of the skin.

Suitable sunscreens include, but are not limited to: inorganic sunscreens, such as titanium dioxide and zinc oxide; organic sunscreens, such as 2-ethylhexyl p-methoxycinnamate; and mixtures thereof.

As mentioned hereinabove, the present invention additionally relates to a method for artificially tanning human skin which comprises applying to the skin dihydroxyacetone and an azole having the structure

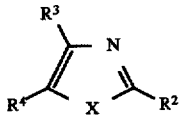

wherein X=S, O, or NR$^1$, and R$^1$ through R$^4$ can be the same or different and are hydrogen; phenyl; $C_1$–$C_6$ alkyl unsubstituted or substituted by phenyl, hydroxyl, carboxy, benzyloxy, amino, halogen, carboxylic acid, sulfonate or phosphonate; or —CH$_2$—CH(COOR')NR"R'" where R', R" and R'" are the same or different and are hydrogen or $C_1$–$C_4$ alkyl.

In a first embodiment of the method of the present invention, the dihydroxyacetone and the azole are substantially simultaneously applied to the skin, for example in a common cosmetically or pharmaceutically acceptable carrier. In a second embodiment the dihydroxyacetone and the azole are sequentially applied to the skin, for example in separate cosmetically or pharmaceutically acceptable carriers. In a third embodiment the azole is applied to the skin before the dihydroxyacetone is applied to the skin.

The following non-limiting examples illustrate various embodiments of the present invention:

EXAMPLE 1

In Vitro Skin Tanning Study

The in vitro reaction between skin tanning agents and amino acids has been shown to be a useful model for the skin tanning reaction in vivo; see L. Goldman et al., "Investigative Studies with the Skin Coloring Agents Dihydroxyacetone and Glyoxal," *The Journal of Investigative Dermatology*, 35, 161 (1960), and references therein. In this model skin tanning ability is correlated with the production of a brown chromagen ($\lambda_{max}$=428 nm), the concentration of which is measured spectrophotometrically.

To 1 mL of an amino acid solution containing 1.0% w/v of either glutamine, glycine, lysine or alanine in pH 7.4 buffered saline solution was added 1 mL of a reactant solution containing 2.0% w/v of either dihydroxyacetone, imidazole or a mixture of both dihydroxyacetone and imidazole (each at 2.0% w/v). The resultant test solutions were allowed to incubate overnight at 37° C., following which time absorbance by each test solution at 428 nm was recorded using a Hewlett Packard Model 8452A UV/VIS spectrophotometer.

For each test solution the absorbance attributable to chromagen production, $A_{chrom}$, is calculated using the formula:

$$A_{chrom} = A_{aa+react} - [A_{aa} + A_{react}]$$

wherein:

$A_{aa+react}$=Absorbance at 428 nm of the test solution $A_{aa}$=Absorbance at 428 nm of the amino acid blank solution $A_{react}$=Absorbance at 428 nm of the reactant blank solution The results are summarized in the following table:

TABLE 1

| Amino Acid | Reactant | $A_{aa+react}$ | $A_{aa}$ | $A_{react}$ | $A_{chrom}$ |
|---|---|---|---|---|---|
| Glutamine | DHA | 0.240 | 0.068 | 0.070 | 0.102 |
| | Imidazole | 0.172 | 0.068 | 0.055 | 0.049 |
| | DHA/Imid.[1] | 2.785 | 0.068 | 0.174 | 2.538 |
| Glycine | DHA | 0.314 | 0.109 | 0.070 | 0.135 |
| | Imidazole | 0.154 | 0.109 | 0.055 | 0 |
| | DHA/Imid.[1] | 5.000 | 0.109 | 0.174 | 4.717 |
| Lysine | DHA | 0.628 | 0.077 | 0.070 | 0.481 |
| | Imidazole | 0.223 | 0.077 | 0.055 | 0.091 |
| | DHA/Imid.[1] | 4.060 | 0.077 | 0.174 | 3.890 |
| Alanine | DHA | 0.174 | 0.075 | 0.070 | 0.029 |
| | Imidazole | 0.164 | 0.075 | 0.055 | 0.034 |
| | DHA/Imid.[1] | 2.890 | 0.075 | 0.174 | 2.641 |

[1]Absorbance values corrected for dilution.

As can be seen from the data in Table 1, the skin tanning reaction between dihydroxyacetone and amino acids is greatly enhanced in the presence of imidazole. Specifically, production of brown chromagen in the presence of imidazole is enhanced 8, 25, 35 and 91 times relative to the reaction between dihydroxyacetone and lysine, glutamine, glycine and alanine, respectively, in the absence of imidazole.

EXAMPLE 2

In Vivo Skin Tanning Study

A total of 7 female volunteers between the ages of 20–50 were selected for a clinical study to assess the skin tanning reaction on skin following sequential treatment with imidazole and dihydroxyacetone. The volunteers were healthy individuals with no evidence of acute or chronic disease including dermatologic or ophthalmologic problems. Pregnant or lactating females were excluded. The test site was devoid of warts, nevi, moles, sunburn, suntan, scars and active dermal lesions.

The right arm of each volunteer was treated with 2 mL of a 1% w/v solution of imidazole in 50% aqueous ethanol. The solution was allowed to absorb into the skin for five minutes. A 3% w/v solution of dihydroxyacetone in 50% aqueous ethanol was then applied to the same site. The left arm of each volunteer was treated with the dihydroxyacetone solution alone.

Skin color was measured using a Minolta Chromameter Model CR200 from both sites before treatment and after 30 minutes, one hour, two hours, five hours and 24 hours. Decrease in reflectance ($\Delta L^*$), increase in red coloration ($\Delta a^*$) and increase in yellow coloration ($\Delta b^*$) were calculated as compared to baseline skin color. Total color change ($\Delta E^*$) was calculated as follows:

$$\Delta E^* = [(\Delta L^*)^2 + (\Delta a^*)^2 + (\Delta b^*)^2]^{1/2}$$

The results are summarized in the following table:

TABLE 2

| Time | $\Delta E^*$ (DHA Treatment) | $\Delta E^*$ (Imidazole + DHA Treatment) |
|---|---|---|
| 30 minutes | 0.85 | 1.98 |
| One hour | 1.16 | 1.69 |
| Two hours | 1.64 | 2.03 |
| Five hours | 2.67 | 4.19 |
| 24 hours | 2.97 | 4.04 |

As can be seen from Table 1, sequential treatment of the skin with imidazole and dihydroxyacetone provides a significantly darker tan than that provided by treatment of the skin with dihydroxyacetone alone. The tan produced by said sequential treatment was natural-looking and visibly observable on the skin after only 30 minutes.

EXAMPLE 3:
SKIN TANNING COMPOSITION

| Ingredient | Percent by Weight |
|---|---|
| Phase 1 | |
| Cetyl Alcohol | 4.0 |
| Stearyl Alcohol | 1.0 |
| Steareth-2 | 1.5 |
| Steareth-21 | 0.5 |
| Coco Caprylate/Caprate | 4.0 |
| $C_{12-15}$ Alcohols Benzoate | 5.0 |
| Laureth-1 | 2.0 |
| Glyceryl Stearate | 3.0 |
| Glyceryl Stearate/PEG Isostearate | 1.0 |
| Propylene Glycol Dipelargonate | 3.0 |
| Phenyl Trimethicone | 5.0 |
| Octyl Palmitate | 4.0 |
| Octyl Hydroxystearate | 2.0 |
| Phase 2 | |
| Purified Water | 15.0 |
| Glycerine | 3.0 |
| Butylene Glycol | 5.0 |
| Imidazole | 1.5 |
| Phase 3 | |
| Purified Water | 33.0 |
| Dihydroxyacetone | 5.0 |
| Imidazolidine Urea | 0.5 |

Procedure

Phase 1 ingredients and Phase 2 ingredients are combined in separate vessels and each heated with stirring to 70° C. The combined Phase 1 is then added with stirring to the combined Phase 2 at 70° C. and the resultant mixture is allowed to cool with stirring to 30° C. The combined Phase 3 ingredients are then added and the resultant final mixture allowed to cool to room temperature to form a nonionic oil-in-water emulsion.

While the present invention has been set forth in terms of specific embodiments thereof, it will be understood that numerous variations are now enabled to those skilled in the art. Accordingly, the invention is to be broadly construed and limited only by the scope of the appended claims.

What is claimed is:

1. A skin tanning composition which comprises:
   (a) dihydroxyacetone;
   (b) an azole having the structure

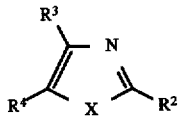

wherein X=S, O, or $NR^1$, and $R^1$ through $R^4$ can be the same or different and are hydrogen; phenyl; $C_1-C_6$ alkyl unsubstituted or substituted by phenyl, hydroxyl, carboxy, benzyloxy, amino, halogen, carboxylic acid, sulfonate or phosphonate; or —$CH_2$—$CH(COOR')NR"R'''$ where R', R" and R''' are the same or different and are hydrogen or $C_1-C_4$ alkyl; and
   (c) a cosmetically or pharmaceutically acceptable carrier.

2. The skin tanning composition of claim 1 wherein the dihydroxyacetone is present in an amount of from about 1 to about 20 percent by weight of the total composition.

3. The skin tanning composition of claim 2 wherein the dihydroxyacetone is present in an amount of from about 3 to about 5 percent by weight of the total composition.

4. The composition of claim 1 wherein the azole is present in an amount of from about 1.5 to about 7.5 percent by weight of the total composition.

5. The composition of claim 4 wherein the azole is present in an amount of from about 1.5 to about 2 percent by weight of the total composition.

6. The composition of claim 1 wherein X=$NR^1$ or S.

7. The composition of claim 6 wherein $R^1$, $R^2$, and $R^3$ are hydrogen.

8. The composition of claim 7 wherein $R^4$ is hydrogen.

9. The composition of claim 7 wherein $R^4$ is —$CH_2$—$CH(COOH)NH_2$.

10. The composition of claim 7 wherein $R^4$ is phenyl.

11. The composition of claim 1 additionally comprising an organic acid.

12. The composition of claim 11 wherein the organic acid is selected from the group consisting of alpha-hydroxyacids and beta-hydroxyacids.

13. The composition of claim 11 wherein the organic acid is selected from the group consisting of citric acid and salicylic acid.

14. The composition of claim 11 wherein the organic acid is present in an amount by weight of the total composition sufficient to lower the pH of the composition to from about 3 to about 5.

15. The composition of claim 11 wherein the organic acid is present in an amount of about 5 percent by weight of the total composition.

16. The composition of claim 1 additionally comprising an antioxidant.

17. The composition of claim 16 wherein the antioxidant is green tea extract.

18. The composition of claim 1 wherein the cosmetically or pharmaceutically acceptable carrier is a hydroalcoholic solution.

19. The composition of claim 1 wherein the cosmetically or pharmaceutically acceptable carrier is an oil-in-water emulsion.

20. The composition of claim 19 wherein the emulsion is nonionic.

21. The composition of claim 1 additionally comprising a colloidal mineral dispersion.

22. The composition of claim 21 wherein the colloidal dispersion contains ions derived from elements selected from the group consisting of sodium, calcium, titanium, rubidium, lanthanum, yttrium, vanadium, cerium and neodymium.

23. The composition of claim 1 additionally comprising a sunscreen.

24. A skin tanning composition which comprises:
(a) from about 1.0 to about 20 percent by weight of the total composition of dihydroxyacetone;
(b) from about 1.5 to about 7.5 percent by weight of the total composition of an azole having the structure

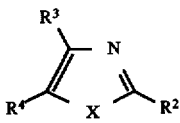

wherein X=S, O, or $NR^1$, and $R^1$ through $R^4$ can be the same or different and are hydrogen; phenyl; $C_1$-$C_6$ alkyl unsubstituted or substituted by phenyl, hydroxyl, carboxy, benzyloxy, amino, halogen, carboxylic acid, sulfonate or phosphonate; or —$CH_2$—$CH(COOR')NR"R"'$ where R', R" and R"' are the same or different and are hydrogen or $C_1$-$C_4$ alkyl;

(c) an organic acid present in an amount by weight of the total composition sufficient to lower the pH of the composition to from about 3 to about 5; and
(d) a cosmetically or pharmaceutically acceptable carrier.

25. The composition of claim 24 wherein X=$NR^1$ or S.

26. The composition of claim 25 wherein $R^1$, $R^2$, and $R^3$ are hydrogen.

27. The composition of claim 26 wherein $R^4$ is hydrogen.

28. The composition of claim 26 wherein $R^4$ is —$CH_2$—$CH(COOH)NH_2$.

29. The composition of claim 26 wherein $R^4$ is phenyl.

30. The composition of claim 24 additionally comprising a colloidal mineral dispersion.

31. The composition of claim 30 wherein the colloidal dispersion contains ions derived from elements selected from the group consisting of sodium, calcium, titanium, rubidium, lanthanum, yttrium, vanadium, cerium and neodymium.

32. A method for artificially tanning human skin which comprises applying to the skin dihydroxyacetone and an azole having the structure

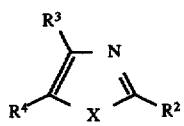

wherein X=S, O, or $NR^1$, and $R^1$ through $R^4$ can be the same or different and are hydrogen; phenyl; $C_1$-$C_6$ alkyl unsubstituted or substituted by phenyl, hydroxyl, carboxy, benzyloxy, amino, halogen, carboxylic acid, sulfonate or phosphonate; or —$CH_2$—$CH(COOR')NR"R"'$ where R', R" and R"' are the same or different and are hydrogen or $C_1$-$C_4$ alkyl.

33. The method of claim 32 wherein the dihydroxyacetone and the azole are substantially simultaneously applied to the skin.

34. The method of claim 32 wherein the dihydroxyacetone and the azole are sequentially applied to the skin.

35. The method of claim 34 wherein the azole is applied to the skin before the dihydroxyacetone is applied to the skin.

36. The method of claim 32 wherein X=$NR^1$ and $R^1$, $R^2$, $R^3$ and $R^4$ are hydrogen.

37. A method for artificially tanning human skin which comprises applying to the skin the composition of claim 1.

38. A method for artificially tanning human skin which comprises applying to the skin the composition of claim 24.

* * * * *